United States Patent [19]

McCoy et al.

[11] Patent Number: 5,090,990

[45] Date of Patent: Feb. 25, 1992

[54] INDUSTRIAL ANTIMICROBIAL:USES FOR 2-(2-BROMO-2-NITROETHENYL)-FURAN

[75] Inventors: William F. McCoy; Scott Thornburgh, both of West Lafayette, Ind.

[73] Assignee: Great Lakes Chemical Corporation, West Lafayette, Ind.

[21] Appl. No.: 615,354

[22] Filed: Nov. 19, 1990

Related U.S. Application Data

[63] Continuation of Ser. No. 205,078, Jun. 10, 1988, abandoned.

[51] Int. Cl.$^5$ ............................................. A01N 43/08
[52] U.S. Cl. ........................................ 71/67; 514/471; 507/132
[58] Field of Search ............................ 71/67; 514/471

[56] References Cited

FOREIGN PATENT DOCUMENTS 7356 5/1954 Fed. Rep. of Germany .
59-184463 9/1984 Japan .

OTHER PUBLICATIONS

Nazarova "Concerning B. Nibovinyl-5-Substituted Furans" Zhur. Cebshcski Khim., vol. 24, 1954, pp. 589-592.
Nazarova et al., "Synthesis of Some Furylnitroolefins with Potential Biological Activity" Potemkin Khim. Form. Zh. Volle, 1972, pp. 629-632.
Gruntfest et al., "Physiochemical Properties and Reactivity"... etc. Zh. Org. Kh., vol. 8, 1972, pp. 405-411.
Latif et al., "Biological Polyactive Compounds, Nitrovinylfurans ... " etc. Journal of Prukt. Chemie., vol. 315, 1973, pp. 419-426.
Schales, et al., "Arylnitroalkenes: A New Group of Antibacterial Agents" J. Am. Chem. Soc. 74, 4486 (1952).

*Primary Examiner*—Richard L. Raymond
*Assistant Examiner*—B. Bembenick
*Attorney, Agent, or Firm*—Woodward, Emhardt, Naughton Moriarty & McNett

[57] ABSTRACT

2-(2-bromo-2-nitroethenyl)-furan can be used as an antimicrobial in broad spectrum of uses. A novel process for preparing 2-(2-bromo-2-nitroethenyl)-furan has been found in which furfural is reacted with bromonitromethane using a primary amine or primary amine salt as a catalytic agent to produce an intermediate product which is dehydrated in the presence of acid to the desired product. An antimicrobial composition comprising 2-(2-bromo-2-nitroethenyl)-furan and a carrier is also disclosed.

18 Claims, 3 Drawing Sheets

EFFICACY OF 2-(2-BROMO-2-NITROETHENYL)-FURAN AGAINST PSEUDOMONAS AERUGINOSA IN PHOSPHATE-BUFFERED WATER AT pH 7.2.

COMPARISON OF ANTIMICROBIAL AGENTS AGAINST PSEUDOMONAS AERUGINOSA IN THE ASTME600-85 PULP AND PAPER EFFICACY TEST.

EFFICACY OF 2-(2-BROMO-2-NITROETHENYL)-FURAN AGAINST NATIVE BACTERIA IN THREE MAJOR CATEGORIES OF METAL-WORKING FLUIDS.

EFFICACY OF 2-(2-BROMO-2-NITROETHENYL)-FURAN AGAINST NATIVE MICROORGANISMS IN THE ASTM E645-85 COOLING WATER BIOCIDE EFFICACY TEST.

COMPARISON OF DISINFECITON KINETICS OF 2-(2-BROMO-2-NITROETHENYL)-FURAN AND β-BROMO-β-NITROSTYRENE (BNS) AGAINST PSEUDOMONAS AERUGINOSA. THE STATISTICAL ANALYSIS SHOWS THAT THERE WAS NO SIGNIFICANT DIFFERENCE IN RATES.

INDUSTRIAL ANTIMICROBIAL USES FOR 2-(2-BROMO-2-NITROETHENYL)-FURAN

This application is a continuation of application Ser. No. 205,078, filed June 10, 1988 (now abandoned).

BACKGROUND OF THE INVENTION

1. Field of the Invention

This invention relates to the novel preparation of 2-(2-bromo-2-nitroethenyl)-furan (BNEF) and to its uses as a broad spectrum antimicrobial agent.

2. Description of the Art

A number of industrial organo-bromine nonoxidizing antimicrobials, including $\beta$-bromo-$\beta$-nitrostryene, are known. Nonoxidizing antimicrobials are used in many industrial systems in which strong oxidizing antimicrobials such as chlorine or bromine cannot be used. Industrial systems generally requiring nonoxidizing antimicrobials include water systems, pulp and paper manufacturing, metal working fluid preservation, latex paint preservation, wood preservation, cosmetics preservation, oil field and institutional hard-surface disinfection. However, despite the many commercially available nonoxidizing antimicrobials, none are entirely suitable for every application due to efficacy, safety, environmental acceptability and cost.

The antimicrobial activity of various 2-furylethylenes, such as 2-(2-nitroethenyl)-furan is also well known. The literature suggests that the microbiocidal activity of the nitroethenylfurans is not sufficient for industrial antimicrobial application unless the furan ring has a 5-nitro substitution. Unfortunately, 5-nitro substituted furan antimicrobials are mutagenic and, in some cases, even carcinogenic in rodents; therefore, 5-nitrofuran derivatives are unsuitable for industrial applications. However, the prior art has failed to recognize the effective antimicrobial activity of 2-(2-bromo-2-nitroethenyl)-furan (BNEF) as an nonoxidizing antimicrobial.

Russian Patent 1,027,663, issued Jan. 1, 1967, discloses the usage of furylnitroalkylenes as antimicrobials. The furylnitroalkyenes are applied to the root zone of a plant or to the soil to control nematodes.

Nazarova and Potemkin in an article entitled "Synthesis of Some Furylnitroolefins with Potential Biological Activity" describe the laboratory preparation of selected furylnitroolefins including BNEF. The process used to prepare BNEF utilizes an 100 percent stoichiometric excess of aqueous potassium hydroxide as a catalytic agent. However, it has been found that the BNEF formed by the described process is undesirably contaminated with nonbrominated nitroethenylfuran, a compound with lower antimicrobial activity.

The Russian article "Physiochemical Properties and Reactivities of Furylnitroolefins" by Gruntfest, et al., discloses the physiochemical properties, structures and reactivities of a series of furylnitroolefins. The article fails to disclose the antimicrobial activities of any of the studied furylnitroolefins.

Japanese Patent 59/184463 discloses a antimicrobial use of nitroethenylfuran used as a component of an antifouling coating for ship bottoms.

Accordingly, a primary object of the present invention is the development of a new broad spectrum industrial antimicrobial agent incorporating 2-(2-bromo-2-nitroethenyl)-furan.

Another object is to obtain a new broad spectrum antimicrobial agent of the character described that is nonoxidizing.

A still further object is to provide an improved process for producing 2-(2-bromo-2-nitroethenyl)-furan which eliminates formation of nonbrominated nitroethenylfuran.

SUMMARY OF THE INVENTION

The foregoing and other objects, advantages and features of the present invention may be achieved by using 2-(2-bromo-2-nitroethenyl)-furan as a broad spectrum industrial antimicrobial agent. More particularly, it has been found that 2-(2-bromo-2-nitroethenyl)-furan can be used in water treatment, pulp and paper manufacturing, metal working fluids, and various other nonoxidizing biocides applications. 2-(2-bromo-2-nitroethenyl)-furan is effective against a wide spectrum of bacteria, algae, and fungi.

It has further been discovered that 2-(2-bromo-2-nitroethenyl)-furan may be produced by a novel process. The novel process greatly eliminates the formation of nonbrominated nitroethenylfuran, an impurity in the product, resulting from the competing reaction initiated by the nucleophilic attack on bromine by the hydroxide ion from the aqueous hydroxide catalytic agent in the reaction. The novel process comprises reacting furfural with bromonitromethane using a primary amine or a primary amine salt and sodium carbonate as the catalytic agent to produce an intermediate, 2-bromo-1-(2-furyl)-2-nitroethanol, which is dehydrated in the presence of acid to the desired product.

DETAILED DESCRIPTION OF THE PREFERRED EMBODIMENTS

Figure 1:
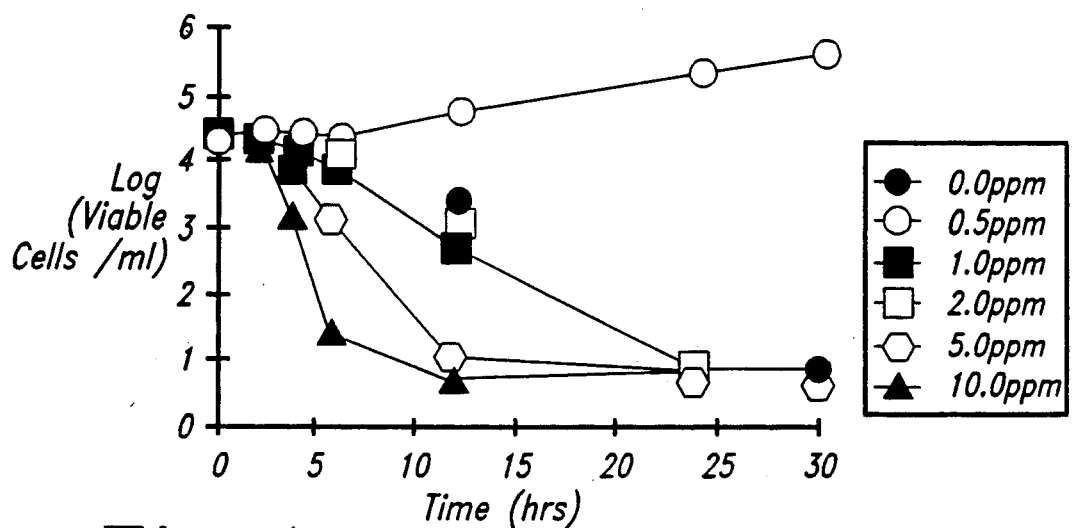
FIG. 1 is a graph showing the relationship between bacterial viability and time in the usage of 2-(2-bromo-2-nitroethenyl)-furan against the most common bacterium found in industrial cooling water.

The present invention relates to new efficacous uses of 2-(2-bromo-2-nitroethenyl)-furan (BNEF) as a versatile chemical antimicrobial agent. BNEF has been shown to be an extremely powerful antimicrobial agent. It is active at low levels against a broad spectrum of microorganisms including bacteria, such as Gram negative bacteria such as *Pseudomonas aeruginosa Xanthomonas prunii, Erwina anylovora,* or *Escherichia coli,* and Gram positive bacteria such as *Bacillus megaterium, Streptococcus pyogenes, Clostridium botulium,* or *Staphylococcus aureus;* algae such as *Chlorella pyrenoidosa* and other green algae, and blue-green algae; and fungi such as *Aspergillus niger, Trichomonas vaginitis, Alternaria solani,* Trichoderma, Saccharomyces, and Rhizoctania. BNEF can be produced from furfural, an inexpensive biodegradable agricultural waste product. Further, BNEF is a strong chromophore and can therefore easily be detected.

The invention also relates to a novel antimicrobial composition. The antimicrobial composition which exists in liquid form comprises a mixture of BNEF and an inert carrier such as lower alcohol, tetrahyrdrofuran, tetrahydrofurfuryl alcohol, N-methylpyrrolidone, and dimethylformamide. Tetrahydrofurfuryl alcohol has been found to be a particularly useful carrier. The mixture comprises 0.1–50% w/v of BNEF and 50–99.9% w/v of carrier. More desirably, the composition comprises 1–50% w/v of BNEF and 50–99% w/v of the carrier. Most desirably, the composition comprises 20% w/v of BNEF and 80% w/v of carrier.

The invention also relates to a novel process of synthesizing BNEF which eliminates the formation of nonbrominated nitroethenylfuran. The process entails contacting furfural, methylammonium hydrochloride and sodium carbonate in a polar solvent. A preferred solvent for use in this invention is ethanol. Bromonitromethane is slowly added to the chilled reaction mixture. The preferred temperature range for the reaction is 0°–10° C. The reaction mixture is agitated until the furfural is consumed and then is acidified. The acidified reaction mixture is stirred until the dehydration is complete. After acidification the reaction mixture may be warmed gently to increase the rate of the dehydration step.

In addition, the invention relates to a method of inhibiting microbial growth in an aqueous media by the addition of BNEF. Possible aqueous media include cooling water, pulp and paper making process flows, metal working fluids, air-washers, oilfield injection water and drilling muds, acrylic latex paint emulsions, adhesives and coatings, swimming pools and spas, and cosmetics. An antimicrobially effective amount of BNEF is added to the aqueous media. An antimicrobially effective amount can be found in the range of approximately 0.5 parts per million (ppm) to 300 ppm.

In general, BNEF is a broad spectrum antimicrobial with a multitude of possible applications. The possible applications can be divided into four groups: nonoxidizing antimicrobial applications; the biocidal applications; applications as a synergist with both other nonoxidizing biocides and oxidizing biocides; and other novel applications. Possible nonoxidizing antimicrobial applications include but are not limited to: water treatment, pulp and paper manufacturing, metal working fluid preservation, fuel preservation, latex paint preservation, cosmetics preservation, and swimming pool and spas applications. BNEF can be used in biocidal applications for mollusks such as Corbicula (clams) and *Oncomelania bulinus* (snails); for protozoa such as Giardia and Entamoeba, and for fungi such as *Trichomonas vaginalis*. Further, BNEF can be used in combination with other nonoxidizing biocides such as, for example, quaternary ammonium salts, isothiazolone biocides, dibromonitrilopropionamide (DBNPA), 2-bromo-2-nitro-propane-1,3-diol, tributyltin oxide, triazine herbicides, 3,3,4,4-tetrachloroterahydrothiophene 1,1-dioxide, methylene bisthiocyanate, or with oxidizing biocides such as: chlorinated isocyanurates, halogenated hydantoins, hypochlorite liquids and solids, chlorine dioxide, hydrogen peroxide, peracetic acid, and ozone.

EXAMPLE

The following example is given to illustrate the process of the invention and should not be construed as limiting its scope.

2-(2-bromo-2-nitroethenyl)-furan with a reduced level of nonbrominated nitroethenylfuran was prepared in the following manner. Furfural (1 mol, 96.09 grams) methylammonium hydrochloride (0.1 mol, 6.7 grams) and sodium carbonate (0.1 mol, 10.5 grams) in 750 milliliters ethanol were placed in a 2 liter flask equipped with an overhead stirrer and an additional funnel. Bromonitromethane (1 mol, 39.89 gram) was added dropwise over a period of 45 minutes. The mixture was stirred for 25 hours at 5° Centigrade. After being stirred, 750 milliliters of chilled water were added to the mixture to dissolve any undissolved salts. The mixture was then slowly added to 720 milliliters of cold 20 percent aqueous hydrochloric acid and the resulting solution was stirred for 2 hours at 5° Centigrade. A dark oil separated from the solution; the organic phase was separated and retained. The aqueous phase was extracted using methylene chloride. The solvent was driven off the extract on a rotary evaporator. The resultant oil was combined with the retained organic layer, and the combined organic phases were steam distilled. The solid product was filtered and recrystalized from ethanol. The product was obtained as bright, yellow crystals.

EXPERIMENTAL EVALUATIONS

It has been found that BNEF is active against a broad spectrum of microorganisms. Table 1 shows the minimum inhibitory concentrations against bacteria and algae for a number of biocidal compounds including BNEF. The data illustrates BNEF is active at very low concentrations.

TABLE 1

Efficacy of 2-(2-bromo-2-nitroethenyl)furan and related compounds against bacteria and algae in laboratory tests.

| | Minimum Inhibitory Conc (ppm) | | |
|---|---|---|---|
| Compounds | *Pseudomonas aeruginosa* | *Baccilus megaterium* | *Chlorella pyrenoidosa* |
| furylethylene | >1000 | >1000 | 250–1000 |
| 3-(2-furyl)acrolein | 250–500 | 250–500 | 16–63 |
| 2-nitro-1-(2-furyl)ethylene | 63–125 | 63–125 | 16–63 |
| 2-(2-bromo-2-nitroethenyl)furan | 5–10 | 5–10 | 4–16 |
| 5-nitro-2-furaldehyde | 6–12 | 3–6 | 4–16 |

FIG. 1 illustrates a decrease in the viability of *Pseudomonas aeruginosa*, a common bacterial genus found in industrial cooling water upon contact with different concentrations of BNEF. The experiment was performed in phosphate buffered water at a pH of 7.2. As seen in the Figure, the efficacy data indicate about 10 ppm of BNEF is required to eliminate 99.9% of the test inoculum after 6 hours of contact.

Figure 2:
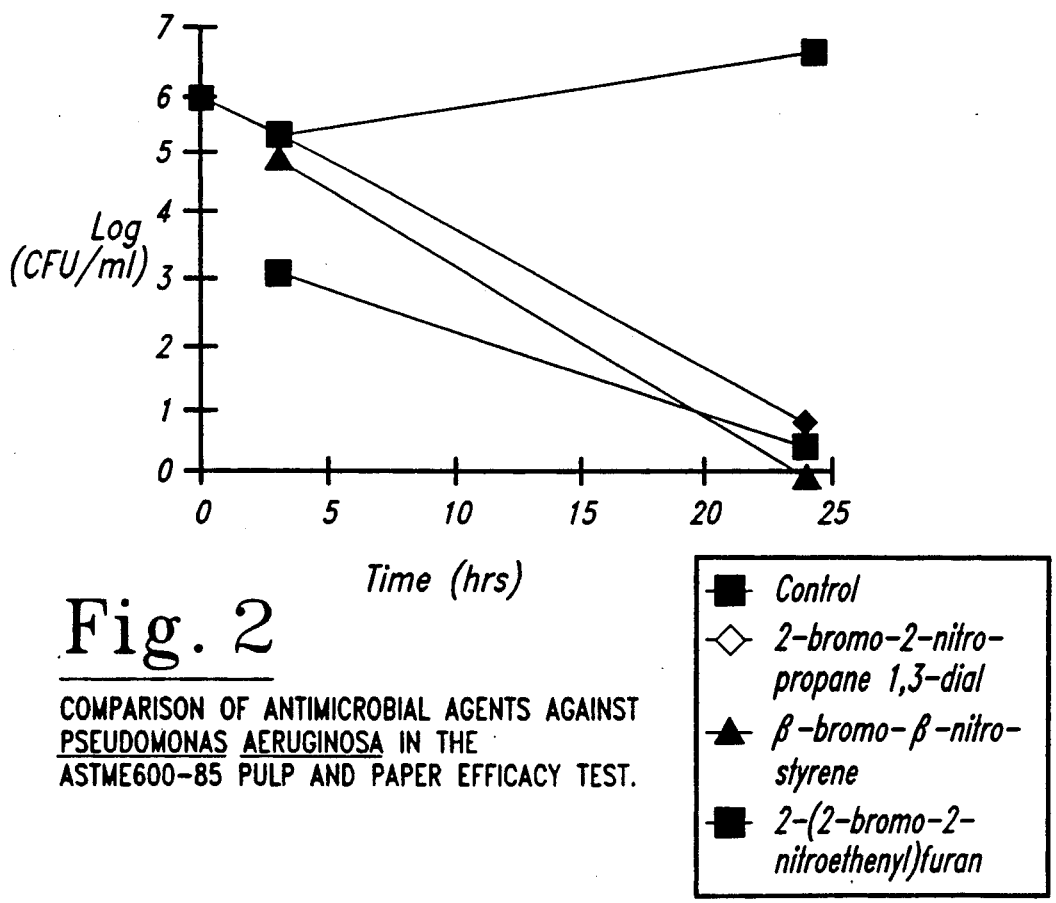
FIG. 2 is a compilation of results from the ASTM E600-85 Pulp and Paper efficacy test.

BNEF can also be used as an antimicrobial in pulp and paper manufacturing applications. FIG. 2 shows results from the ASTM Pulp and Paper efficacy test (ASTM E600-85). This laboratory test indicates that BNEF is at least as active as two commercially successful antimicrobials currently used in this industry.

Figure 3:
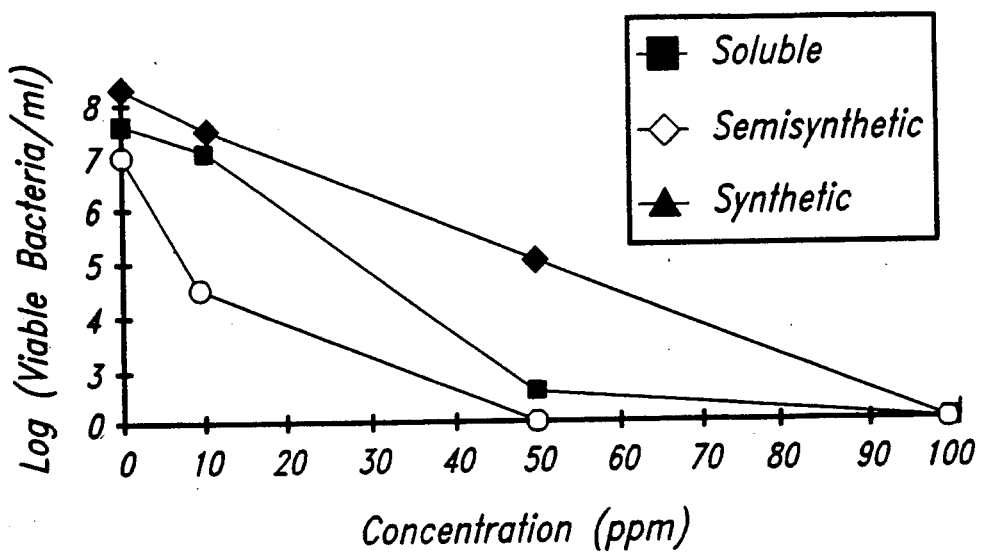
FIG. 3 is a graph showing the relationship between bacterial viability and concentration of 2-(2-bromo-2-nitroethenyl)-furan in the three major categories of metal working fluid.

In addition to pulp and paper manufacturing, BNEF can be used as a metal working fluid preservative. Test data show BNEF is effective in three categories of metal working fluids (soluble oil, semisynthetic, and synthetic) against bacteria, as seen in FIG. 3, and fungi. These tests were performed in the following manner. A typical soluble oil, semi-synthetic, and synthetic metalworking fluid were prepared with tap water at a ratio of 20:1. A field sample of "spoiled" fluid was mixed with a nutrient broth (50/50) and incubated for 2% hours to serve as the bacterial inoculum. Fungi isolated from metalworking fluids were grown on agar plates. The fungi were harvested into a suspension which then served as the fungal inoculum. At time zero, 50 ml aliquots of each fluid were prepared. The fluids were inoculated and dosed with the antimicrobial agent at different concentrations. Time zero bacterial and fungal counts were taken on each control fluid. The samples were then placed on a mechanical shaker (at room temperature) for 72% hours. Bacterial and fungal counts were then performed. The preferred level of BNEF in this application is in the range of 10 to 100 ppm.

Figure 4:
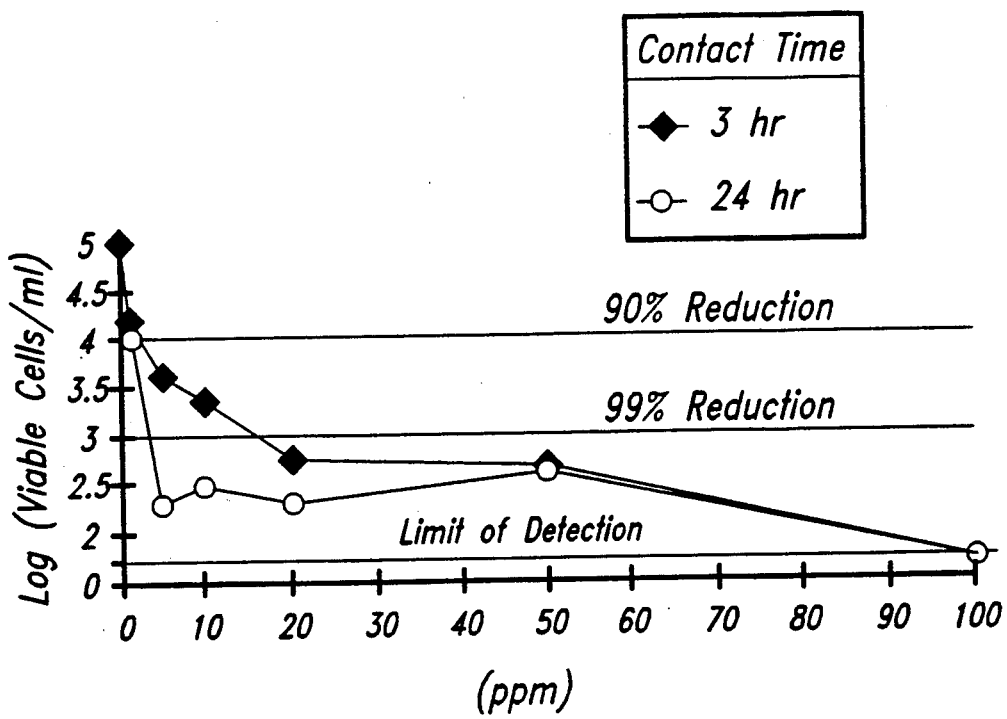
FIG. 4 is a graph showing the efficacy of 2-(2-bromo-2-nitroethenyl)-furan in industrial cooling water applications according to the ASTM E-645-85 method.

BNEF can also be used in water treatment such as for example treatment of industrial cooling water. FIG. 4 shows the efficacy of BNEF in industrial cooling water. As seen from the Figure, approximately a 99 percent reduction in viability of naturally occurring microorganism in industrial cooling water can be achieved with the application of 5 ppm of BNEF and 24 hours of contact. Shorter contact times require a higher concentration of BNEF in the application. Preferably an antimicrobially effective amount of BNEF should be added to reduce the viability of microorganisms by at least 90 percent. It is especially preferred to employ about 1 ppm to about 5 ppm of BNEF.

Figure 5:
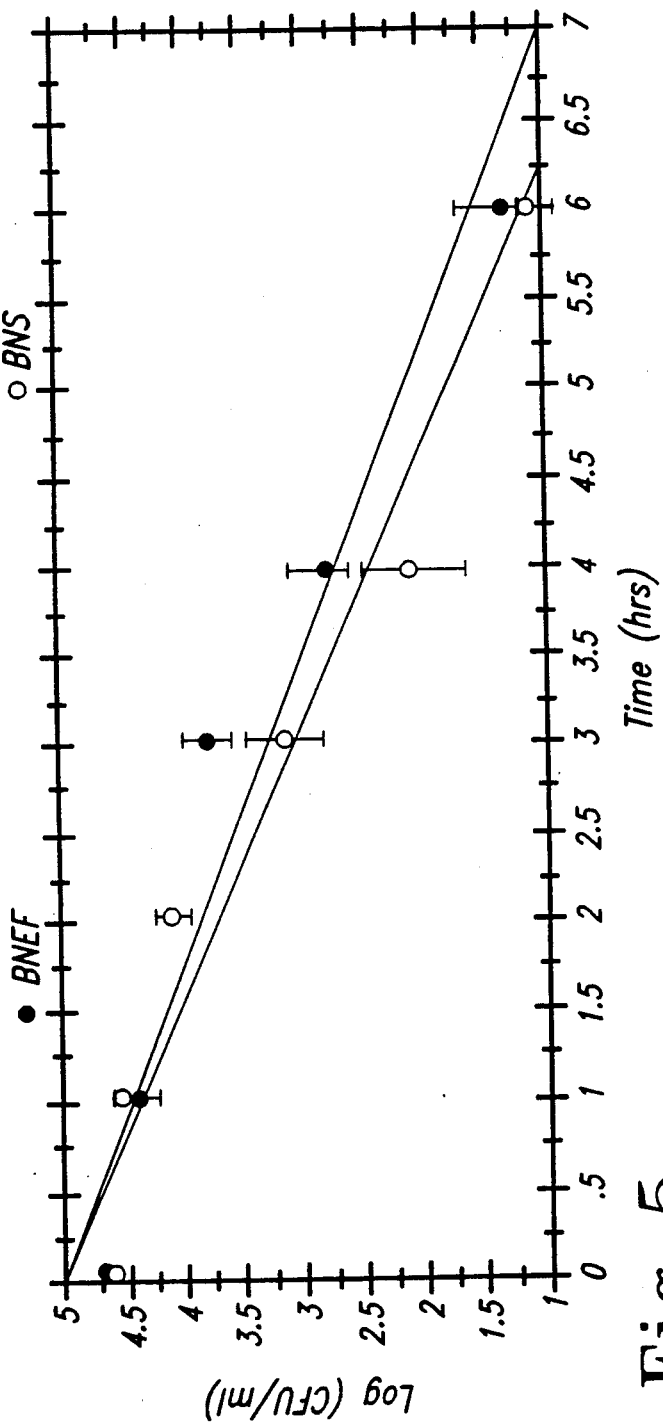
FIG. 5 is a graph showing the kinetics of disinfection of 2-(2-bromo-2-nitroethenyl)-furan in comparison to its styrene analogue.

FIG. 5 shows the kinetics of disinfection of 10 ppm (w/v) BNEF in comparison to its styrene analogue, $\beta$-bromo-$\beta$-nitrostyrene, a successful commercial water treatment antimicrobial in a phosphate buffer at a pH of 7.0. The data were analyzed statistically and demonstrate BNEF is as effective as an antimicrobial in water treatment application as $\beta$-bromo-$\beta$-nitrostyrene.

Virtually all modern water treatment applications are alkaline. Even in an alkaline condition, BNEF is quite active. Data In Table 2 show the contact time of BNEF required for a 99.9% reduction in viability of *Pseudomonas aeruginosa* in water. The data were acquired in the following manner. Several pure culture cell suspensions of *Pseudomonas aeruginosa* were prepared in phosphate-buffered water that had been adjusted to pH 7.0 or pH 8.1. The initial concentration of viable cells was determined by counting colony forming-units in the standard spread plate method. A tetrahydrofurfuryl alcohol (THFA) solution containing the antimicrobial (90% THFA, 10% antimicrobial) was added to cell suspensions at each pH such that 10 ppm of the antimicrobial was dosed. Similarly, THFA was added without antimicrobial to cell suspensions at each pH value to serve as no-treatment controls. The concentration of viable cells was then determined at regular time intervals for all of the cell suspensions until at least 99.9% reduction in viability (compared to the controls) was achieved by the antimicrobial treatment.

TABLE 2

| Contact time of 10 ppm of 2-(2-bromo-2-nitroethenyl)-furan required for 99.9% reduction in viability of *Pseudomonas aeruginosa* in water. | | |
|---|---|---|
| pH | Initial Cell Concentration | Required Contact Time (99.9% reduction) |
| 7.0 | $3.2 \times 10^4$ | 5 hrs. |
| 8.1 | $\sim 1.0 \times 10^4$ | 1 hrs |

The data in Table 2 suggest that the disinfection rate for BNEF at a concentration of 10 ppm is actually faster at a pH level of 8 as compared to the disinfection rate at a pH level of 7. Therefore, the effect of increased pH on the efficacy of BNEF in water applications appears to be favorable. Increased disinfection rate with higher pH is also found in $\beta$-bromo-$\beta$-nitrostyrene, a commercially successful analog of BNEF.

Table 3 shows the minimum inhibitory concentration of BNEF against various microorganisms, in addition to *Pseudomonas aeruginosa* and *Bacillus megaterium* discussed earlier, encountered in various water treatment applications. The data show the compound has a broad spectrum in its activity. All of the minimum inhibitory concentration determinations were made in a nutrient-rich growth medium in the following manner. Each organism was inoculated into a nutrient-rich medium that supported its growth. Various concentrations of a solution of the antimicrobial in THFA (90% THFA, 10% antimicrobial) were dosed into the inoculated growth medium; inoculated media were also dosed only with THFA (no antimicrobial) to serve as controls. Two concentrations of antimicrobial were recorded for each organism after growth in the controls was visible (the lowest concentration that prevented growth and the highest concentration that allowed growth); the MIC is reported as the range between these concentrations.

The data in Table 3 are significant because they show an extraordinary spectrum of activity for this antimicrobial; broad-spectrum of activity is clearly an advantage for applications of industrial antimicrobials.

TABLE 3.

| Minimum inhibitory concentration against various microorganisms. | | |
|---|---|---|
| Organism | Type of Microorganism | MIC(ppm) |
| *Staphylococcus aureus* | Bacterium | 3.0–7.6 |
| *Xanthomonas prunii* | Bacterium | 2.0–5.0 |
| *Xanthomonas palargonii* | Bacterium | 1.0–2.0 |
| *Xanthomonas poinsettiácola* | Bacterium | 0.5–1.0 |
| *Erwina chysanthemi* | Bacterium | 0.5–1.0 |
| *Erwina anylovora* | Bacterium | <0.5 |
| *Erwina caratovora* | Bacterium | 0.5–1.0 |
| *Agrobacterium tumefaciens* | Bacterium | 0.5–1.0 |
| *Photobacterium phosphoreum* | Bacterium | 1.0–5.0 |
| *Desulfovibro desulfuricans* | Bacterium | <2.0 |
| *Alternaria solani* | Fungus | <1.0 |
| *Aspergillus niger* | Fungus | <1.0 |
| *Saccharomyces sp.* | Fungus (yeast) | <3.0 |

TABLE 3.-continued

Minimum inhibitory concentration against various microorganisms.

| Organism | Type of Microorganism | MIC(ppm) |
|---|---|---|
| Trichoderma virde | Fungus | <5.0 |
| Rhizoctonia sp. | Fungus | <1.0 |
| Chlorella pyrenoidosa | Algae | 4–16 |

The following analogues of 2-(2-bromo-2-nitroethenyl)-furan listed in Table 4, have been synthesized and tested for antimicrobial efficacy. All of these compounds are active in the low ppm range against *Pseudomonas aeruginosa*. These compounds were also tested in the pulp and paper ASTM efficacy test and shown to be active at low levels. None of the compounds tested appear to be more active than 2-(2-bromo-2-nitroethenyl)-furan.

TABLE 4.

Minimum inhibitory concentration of 2-(2-bromo-2-nitroethenyl)-furan analogues against *Pseudomonas aeruginosa*

| Compound | MIC* Against Pseudomonas aeruginosa (ppm) |
|---|---|
| 5-nitro-2-(2-bromo-2-nitroethenyl)-furan | 8–16 |
| 5-bromo-2-(2-bromo-2-nitroethenyl)-furan | 10–20 |
| 5-methyl-2-(2-bromo-2-nitroethenyl)-furan | 21–42 |
| 2-(2-bromo-2-nitroethenyl)-thiophene | 21–42 |

*MIC - Minimum Inhibitory Concentration

We claim:

1. A method for inhibiting microbial growth in an aqueous media which comprises adding an antimicrobially effective amount of 2-(2-bromo-2-nitroethenyl)-furan thereto.

2. The method of claim 1 wherein the microbial growth is bacterial.

3. The method of clam 2 wherein the bacterium is selected from the group of bacteria consisting of Gram negative and Gram positive bacteria.

4. The method of claim 3 wherein the Gram negative bacteria is chosen from the group of Pseudomonas and pseudomonads, Xanthomonous, Erwinia, Agrobacterium, Photobacterium, and Desulfovibrio.

5. The method of claim 3 wherein the Gram positive bacteria is chosen from the group of Bacillus, staphylococcus, Streptococcus, and Clostridium.

6. The method of claim 1 wherein the microbial growth is algae.

7. The method of claim 6 wherein the algae is *Chlorella pyrenoidosa*.

8. The method of claim 1 wherein the microbial growth is a fungus.

9. The method of claim 8 wherein the fungus is chosen from the group of fungi consisting of Aspergillus, Trichomonas, Alternaria, Trichoderma, Saccharomyces, and Rhizoctonia.

10. The method of claim 1 wherein the aqueous media is selected from the group consisting of cooling water, metal working fluids, air-washers, oilfield injection water and drilling muds, acrylic latex paint emulsions, adhesives and coatings, swimming pools and spas, and cosmetics.

11. The method of claim 1 which comprises adding an antimicrobially effective amount in the range of 0.5 ppm to 300 ppm.

12. A method for inhibiting microbial growth selected from the group consisting of algae, fungi and bacteria in an aqueous media which comprises adding an antimicrobially effective amount in the range of 0.5 ppm to 300 ppm of 2-(2-bromo-2-nitroethenyl)-furan, a broad spectrum antimicrobial agent, thereto.

13. A method as claimed in claim 12 wherein the bacterium is selected from the group of bacteria consisting of Gram negative and Gram positive bacteria.

14. A method as claimed in claim 13 wherein the Gram negative bacteria is chosen from the group of Pseudomonas and pseudomonads, Xanthomonous, Erwinia, Agrobacterium, Photobacterium, and Desulfovibrio.

15. A method as claimed in claim 13 wherein the Gram positive bacteria is chosen from the group of Bacillus, Staphylococcus, Streptococcus, and Clostridium.

16. A method as claimed in claim 12 wherein the algae is *Chlorella pyrenoidosa*.

17. A method as claimed in claim 12 wherein the fungus is chosen from the group of fungi consisting of Aspergillus, Trichomonas, Alternaria, Trichoderma, Saccharomyces, and Rhizoctonia.

18. A method as claimed in claim 12 wherein the aqueous media is selected from the group consisting of pulp and paper making process flows, cooling water, metal working fluids, air-washers, oilfield injection water and drilling muds, acrylic latex paint emulsions, adhesives and coatings, swimming pools and spas, and cosmetics.

* * * * *

UNITED STATES PATENT AND TRADEMARK OFFICE
CERTIFICATE OF CORRECTION

PATENT NO.   :   5,090,990

DATED        :   February 25, 1992

INVENTOR(S)  :   William F. McCoy, Scott Thornburgh

It is certified that error appears in the above-identified patent and that said Letters Patent is hereby corrected as shown below:

In Column 4, line 13 change "39.89 gram" to --139.89 gram--.

In Column 5, line 17 change "2% hours" to --24 hours--.

In Column 5, line 27 change "72% hours" to --72 hours--.

In Column 7, line 47 change "clam 2" to --claim 2--.

Signed and Sealed this

Thirty-first Day of August, 1993

Attest:

BRUCE LEHMAN

*Attesting Officer*       *Commissioner of Patents and Trademarks*